United States Patent [19]

Morales et al.

[11] Patent Number: 5,146,034
[45] Date of Patent: Sep. 8, 1992

[54] CONVERSION OF PARAFFINS TO OLEFINS

[75] Inventors: Edrick Morales; Anne M. Gaffney; John A. Sofranko, all of West Chester, Pa.

[73] Assignee: Arco Chemical Technology, L.P., Wilmington, Del.

[21] Appl. No.: 793,756

[22] Filed: Nov. 18, 1991

[51] Int. Cl.$^5$ ............................................. C07C 5/333
[52] U.S. Cl. ................................... 585/654; 585/661; 208/135
[58] Field of Search ............... 585/654, 660, 661, 440, 585/444; 208/136, 137, 138, 135

[56] References Cited

U.S. PATENT DOCUMENTS

| | | | |
|---|---|---|---|
| 3,140,249 | 7/1964 | Plank et al. | 208/120 |
| 3,899,544 | 8/1975 | Chang et al. | 260/668 C |
| 3,972,832 | 8/1976 | Butter et al. | 252/437 |
| 4,263,129 | 4/1981 | Chen et al. | 208/111 |
| 4,849,567 | 7/1989 | Dessau et al. | 585/660 |

*Primary Examiner*—Theodore Morris
*Assistant Examiner*—William C. Diemler
*Attorney, Agent, or Firm*—William C. Long

[57] ABSTRACT

The present invention relates to the improved dehydrogenation of paraffins using as catalyst zeolite modified with a Group I A modifier and containing a transition metal component.

5 Claims, No Drawings

CONVERSION OF PARAFFINS TO OLEFINS

BACKGROUND OF THE INVENTION

1. Field of the Invention

The present invention relates to the conversion of paraffins to olefins while suppressing undesirable cracking. In particular, the invention provides for the dehydrogenation of paraffin hydrocarbon using zeolite catalysts modified with a Group IA modifier and having incorporated therewith a transition metal component such as Zn.

2. Background of the Invention

The use of aluminosilicate zeolites such as ZSM-5 for the cracking of paraffin hydrocarbons is known. See, for example, U.S. Pat. No. 3,140,249.

The modification of a zeolite such as ZSM-5 by treatment with phosphorous and with the further incorporation therein of a transition metal such as zinc is known. See U.S. Pat. No. 3,972,832. When used for the conversion of a paraffin such as n-hexane cracking to lower olefins and paraffins was achieved.

The preparation of low acidity zeolites such as the sodium form of ZSM-5 and the use of those materials in the conversion of hydrocarbons is known. U.S. Pat. No. 4,263,129 shows the preparation of such catalysts including catalysts also containing a hydrogenation component such as cobalt-molybdenum or nickel-tungsten. The catalysts are described as effective in hydrocracking and result in lower yields of light gaseous hydrocarbons.

U.S. Pat. No. 3,899,544 describes the preparation of modified ZSM-5 catalysts by incorporating a limited amount of a Bronstead or Lewis base such as sodium therein. Hydrogenation/dehydrogenation components such as zinc and cadmium can also be incorporated in the catalysts. The use of catalysts for the conversion of alcohols and ethers to hydrocarbons is taught.

BRIEF DESCRIPTION OF THE INVENTION

In accordance with the present invention, improved dehydrogenation of paraffin hydrocarbons is achieved while the cracking of the paraffin to lower products is substantially suppressed by converting the paraffin using as catalyst a zeolite such as ZSM-5 which has been modified by a Group IA modifier and which has incorporated therein a transition metal component such as Zn. Catalysts such as those described in U.S. Pat. No. 3,899,544 are conveniently used.

DETAILED DESCRIPTION

Paraffin hydrocarbons which are dehydrogenated in accordance with the present invention are linear or branched paraffins, preferably those having 2 to 20 carbon atoms, more preferably those having 2 to 5 carbon atoms. Examples are ethane, propane, n-butane, isobutane, n-pentane, 2-methyl butane, and the like.

In practice of the present invention elevated dehydrogenation reaction temperatures are employed, preferably in the range 500°–700° C. Generally, the temperature should not exceed about 750° C. Normal dehydrogenation pressures ranging from about atmospheric to 1,000 psig are conveniently employed. Space velocities of the order of about 1 to about 10,000 hr.$^{-1}$ WHSV are employed, preferably 10 to 1000 hr.$^{-1}$ WHSV.

Preferably, feed paraffin in the vapor phase is contacted at reaction conditions with solid, modified ZSM-5 catalyst. The dehydrogenation vapor feed can contain, in addition to the paraffin to be dehydrogenated, inert gas and/or steam although the use of these materials is not necessary or preferred.

The catalysts which are used in carrying out the present invention are zeolites such as ZSM-5 which have been modified by the incorporation therein of small but critical amounts of one or more modifiers of Group I A elements and which also contain a transition metal such as Zn. Examples of the Group I A elements include lithium, sodium, potassium, cesium, and the like. Preferred alkali metal modified catalysts are those prepared as described in U.S. Pat. No. 3,899,544.

In accordance with the invention, the modifier is incorporated with the ZSM-5 in an amount sufficient to substantially, but not completely, neutralize the acidic ZSM-5 sites. Generally it is advantageous to neutralize 30 to 85% of the cation sites. Preferably, this is accomplished by incorporating at least about 1% by weight of the modifying element in the ZSM-5 up to about 5% by weight.

In one embodiment, H ZSM-5 is impregnated or ion-exchanged with a solution of a compound of the modifier and by ion exchange an appropriate amount of modifier is incorporated in the ZSM-5. Alternatively, the ZSM-5 in, for example, the Na form is incompletely converted to H ZSM-5 by treatment with ammonium chloride and the like. Still further, the H ZSM-5 can be combined with a matrix which contains the modifier to form a suitable final catalyst composition.

It is believed that the acidic sites of H ZSM-5 provide the active sites for hydrocarbon conversion but that where there are only acid sites reactions such as cracking and the like tend to predominate. By incorporating the designated modifiers in the ZSM-5, the catalyst remains active for hydrocarbon conversion, but cracking of paraffin feed is greatly reduced.

In addition to the Group I A modifier, there is also incorporated in the catalyst a transition metal from Groups III–XII. Examples of suitable transition metals are Zn, V, Cr, Mn, Fe, Co, Ni, Cu, Mo and the like.

It is preferred to first prepare the Group I A modified zeolite as above described and subsequently to impregnate the modified zeolite with the desired amount of compound of the transition metal followed by calcining to produce the final catalysts.

Generally, amounts of transition metal, expressed as the element in the range of 1–20 wt. % of the final catalyst are suitable, preferably 2–10 wt. %.

The following examples illustrate the invention:

H-ZSM-5 was subjected to ion exchange treatment with an aqueous NaOH solution. The resulting ZSM-5 was dried at 110° C. and calcined at 550°–1000° C. The resulting product contained 1 wt. % Na.

A portion of the Na containing ZSM-5 was impregnated with an aqueous Zn carbonate solution dried and calcined at 550°–1000° C. to produce a ZSM-5 product containing 1 wt. % Na which also contained 5 wt. % Zn.

A series of runs were made to evaluate the effectiveness of the catalyst in dehydrogenation of paraffins. Conditions of the runs and the results achieved are shown in the following table along with comparative results with simple steam pyrolysis, with Na ZSM-5 containing no Zn and with Zn ZSM-5 containing no Na.

TABLE 1

| | \multicolumn{6}{c}{Run} | | | | | |
|---|---|---|---|---|---|---|
| | A | B | C | D | E | F |
| Temp., °C. | — | 647 | 608 | 634 | 675 | 674 |
| Paraffin | isobutane | isobutane | isobutane | isobutane | propane | propane |
| WHSV, $h^{-1}$ | — | 71 | 71 | 71 | 11 | 11 |
| Conversion, % | 50.0 | 20.4 | 87.8 | 51.9 | 18 | 52.8 |
| Selectivity, % for: | | | | | | |
| coke | — | 4.7 | 1.1 | 2.1 | 22.0 | 16.4 |
| $CH_4$ | 16.4 | 11.5 | 10.8 | 3.3 | 13.8 | 5.4 |
| $C_2H_4$ | 4.2 | 0.7 | 12.7 | 0.9 | 25.5 | 7.3 |
| $C_3H_6$ | 30.4 | 32.9 | 27.3 | 9.27 | 32.7 | 50.8 |
| isobutylene | 34.9 | 25.6 | 7.6 | 46.7 | — | — |
| n-butenes | 3.9 | 21.1 | 11.3 | 27.1 | — | — |
| BTX | — | 0.2 | 20.1 | 3.6 | 0.3 | 14.0 |

Of the above runs, Runs D and F were in accordance with the present invention and employed 5 wt. % Zn impregnated on ZSM-5 which contained 1 wt. % Na.

Run A is illustrative of steam pyrolysis of isobutane.

Runs B and E are comparative and used ZSM-5 which contained 1 wt. % Na but no Zn.

Run C is comparative and used ZSM-5 which contained 6 wt % Zn but no Na.

From the above results it can be seen that in accordance with the invention (Run D) much less cracking took place as compared with steam pyrolysis (Run A), with conversion using ZSM-5 which contained Na but no Zn (Run B) and with conversion using ZSM-5 which contained Zn but no Na (Run C). Run B conversion was lower. Run C conversion was higher, but aromatics production was much greater.

In the conversion of propane, practice of the invention (Run F) gave much higher conversion and less cracking than a comparative run (Run E) using ZSM-5 which contained Na but no Zn.

We claim:

1. The process for the dehydrogenation of a paraffin hydrocarbon having 2 to 20 carbon atoms to the corresponding olefin which comprises contacting the said paraffin with a solid zeolite catalyst consisting essentially of ZSM-5 modified with a Group I A modifier and containing 1–20 wt. % Zn, wherein the dehydrogenation is carried out at a temperature of 500°–700° C. and at a pressure of from atmospheric to 1,000 psig.

2. The process of claim 1 wherein the said modifier is Na.

3. The process of claim 1 wherein said paraffin has 2 to 5 carbon atoms.

4. The process of claim 1 wherein isobutane is dehydrogenated to isobutylene.

5. The process of claim 1 wherein propane is dehydrogenated into propylene.

* * * * *